(12) United States Patent
Breton et al.

(10) Patent No.: US 9,393,266 B2
(45) Date of Patent: *Jul. 19, 2016

(54) BACTERIAL EXTRACTS CULTURED IN THERMAL WATERS FOR REDUCING BAGS AND/OR DARK CIRCLES AROUND THE EYES

(75) Inventors: Lionel Breton, Versailles (FR); Audrey Gueniche, Rueil Malmaison (FR)

(73) Assignee: L'Oreal, Paris (FR)

( * ) Notice: Subject to any disclaimer, the term of this patent is extended or adjusted under 35 U.S.C. 154(b) by 1250 days.

This patent is subject to a terminal disclaimer.

(21) Appl. No.: 12/175,119

(22) Filed: Jul. 17, 2008

(65) Prior Publication Data

US 2009/0028826 A1 Jan. 29, 2009

Related U.S. Application Data

(60) Provisional application No. 60/929,970, filed on Jul. 19, 2007.

(30) Foreign Application Priority Data

Jul. 17, 2007 (FR) ...................................... 07 56535

(51) Int. Cl.
| | | |
|---|---|---|
| *A61K 35/00* | (2006.01) | |
| *A61K 35/66* | (2015.01) | |
| *A61K 35/74* | (2015.01) | |
| *A61K 35/08* | (2015.01) | |
| *A61K 8/99* | (2006.01) | |
| *A61Q 19/00* | (2006.01) | |
| *A61Q 19/02* | (2006.01) | |

(52) U.S. Cl.
CPC . *A61K 35/08* (2013.01); *A61K 8/99* (2013.01); *A61K 35/74* (2013.01); *A61Q 19/005* (2013.01); *A61Q 19/02* (2013.01); *A61K 2800/782* (2013.01)

(58) Field of Classification Search
CPC .......... A61K 35/08; A61K 8/99; A61K 35/74
See application file for complete search history.

(56) References Cited

U.S. PATENT DOCUMENTS

| 4,419,449 A | 12/1983 | Maillard et al. |
|---|---|---|
| 5,536,410 A * | 7/1996 | Kitatsuji ................... C02F 1/54 210/626 |
| 5,618,707 A * | 4/1997 | Homann ................... C12P 7/42 435/120 |
| 5,795,574 A * | 8/1998 | Breton et al. ................. 424/115 |
| 5,919,672 A * | 7/1999 | Homann ............... C07D 205/08 435/121 |
| 6,133,001 A * | 10/2000 | Homann ................. C12P 17/10 435/121 |
| 6,190,671 B1 | 2/2001 | Aubert et al. |
| 6,242,229 B1 * | 6/2001 | Pineau et al. ................. 435/170 |
| 7,279,320 B1 * | 10/2007 | Parker .................... A61K 39/07 435/252.1 |
| 2004/0175407 A1 * | 9/2004 | McDaniel ................ A62D 3/02 424/423 |
| 2006/0147423 A1 * | 7/2006 | Legendre et al. ............ 424/93.4 |
| 2008/0025931 A1 * | 1/2008 | Pelletier et al. ................. 424/59 |
| 2010/0068299 A1 * | 3/2010 | van der Krieken .... A01N 41/04 424/638 |
| 2010/0136132 A1 * | 6/2010 | van der Krieken .... A01N 41/04 424/604 |

FOREIGN PATENT DOCUMENTS

| FR | 2 693 654 | | 1/1994 |
|---|---|---|---|
| JP | 57146792 A | * | 9/1982 |

OTHER PUBLICATIONS

PR Newswire: Is 40+ The New Dating Prime?; PR Newsire, New York, Aug. 24, 2006, 3 pages.*
XP009091787, 2006 ESDR Abstract, #578, www.jidonline.org.

* cited by examiner

*Primary Examiner* — Patricia A Leith
(74) *Attorney, Agent, or Firm* — Buchanan Ingersoll & Rooney PC

(57) ABSTRACT

Bags and/or dark circles around the eyes of individuals afflicted therewith are reduced by administering to such individuals thus effective amounts of at least one extract of a non-photosynthetic and non-fruiting filamentous bacterium cultured in a medium which includes at least one non-sulfurous mineral and/or thermal water, e.g., an extract derived from the bacterium *Vitreoscilla filiformis*, in particular the strain ATCC 15551, cultured in a medium enriched with water from La Roche Posay.

7 Claims, No Drawings

BACTERIAL EXTRACTS CULTURED IN THERMAL WATERS FOR REDUCING BAGS AND/OR DARK CIRCLES AROUND THE EYES

CROSS-REFERENCE TO PRIORITY/PROVISIONAL APPLICATIONS

This application claims priority under 35 U.S.C. §119 of FR 0756535, filed Jul. 17, 2007, and of U.S. Provisional Application No. 60/929,970, Jul. 19, 2007, each hereby expressly incorporated by reference and each assigned to the assignee hereof.

CROSS-REFERENCE TO COMPANION APPLICATIONS

Companion U.S. patent application Ser. No. 12/175,072, filed Jul. 17, 2008; application Ser. No. 12/175,108, filed Jul. 17, 2008; and application Ser. No. 12/175,129, filed Jul. 17, 2008, filed concurrently herewith, each hereby also expressly incorporated by reference and each also assigned to the assignee hereof.

BACKGROUND OF THE INVENTION

1. Technical Field of the Invention

The present invention relates to the care and/or making-up of the contour of the eyes, in particular the care and/or making-up of dark circles around the eyes.

The present invention also relates to the administration of bacterial extracts cultured in thermal water as an agent in an eye contour care and/or makeup composition, as an agent useful for reducing bags and/or dark circles around the eyes.

Preferably, the extract is derived from the bacterium *Vitreoscilla filiformis*, in particular the strain ATCC 15551, cultured in a medium enriched with water from La Roche Posay.

2. Description of Background and/or Related and/or Prior Art

The eye contour, due to its structure and its high innervation, is an anatomical site that is particularly sensitive to environmental factors (UV rays, pollution, tobacco, etc.) and physiological factors (fatigue, stress, etc.). The eye contour has a very important aesthetic role since it immediately reflects fatigue, humor and age.

In humans, the eyes blink a thousand times per day; the epidermis which surrounds them is very thin and not very well irrigated, all these factors facilitate the rapid appearance of wrinkles, fine lines, dark circles and bags. Furthermore, in order to allow significant mobility, the skin of the eyelids is extremely thin (0.33 to 0.36 mm, i.e., 3 to 5 times thinner than the rest of the skin of the face). Easily dehydrated and subjected to external aggressions, the skin of the eye contour requires particular care.

More or less colored or pronounced, dark circles are, depending on the case, the expression of great tiredness, a lack of sleep, a stressful life, or even an illness. Dark circles also have a vascular or hereditary origin.

The eyelids are the reflection of lifestyle: heat, stress, tobacco, UV rays, and facial expressions lead to multiple variations throughout the day.

These variations concern vascularization, hydration and turgescence of the tissues and explain the principal changes observed: swelling, dark circles, fine lines, etc.

The skin of the eye contour is very reactive due to its richness in inflammatory cells (mast cells); which is in fact a site subject to intolerance and allergy reactions.

Furthermore, the skin of the eye contour is particularly sensitive to solar radiation. Excessive exposure without protection can lead to redness, sensitivity, or even swelling via microcirculation disorders. In the long term, the skin of the contour of the eyes undergoes photoaging phenomena.

Surface vascularization is barely visible, since the capillaries have a low flow rate, but the vessels of the subcutaneous layers constitute a large vascular reserve which may vary throughout the day.

The dark circles may be temporary. They correspond to a transitory or permanent vascular congestion which results in hyperpigmentation of the skin. These are always accentuated by tobacco, the abuse of alcohol, stress and fatigue.

The formation of dark circles is especially due to a slowing of the blood microcirculation, especially during the night, that leads to an accumulation of blood pigments in the conjunctive tissue, especially visible on rising in the morning.

Furthermore, the lymphatic system, also slowed down during the night, leads to swelling of the eyelids. This swelling, associated with age-related slackening of the tissues, causes the formation of bags.

Dark circles and bags have always been considered as unattractive and it has always been a goal to mask them or even eliminate them.

In particular, there are makeup products which make it possible to conceal or attenuate, via an optical effect, skin defects such as spots, wrinkles and fine lines. Foundation compositions, for example, generally have the objective of unifying the complexion; they give a matte appearance to the skin that results from a light-diffusing ability at the surface of the skin. But certain compositions may have the drawback of not providing the skin with a natural appearance by giving it a powdery or even plastery appearance and of accentuating skin defects. And certain compositions may be drying in the long term and/or difficult to apply.

Need therefore exists to conceal or blur the defects of the contour of the eyes, in particular of bags and/or dark circles around the eyes, with compositions that make it possible to obtain a uniform and homogeneous complexion of natural, luminous and vibrant appearance, these compositions furthermore being very comfortable after application to the skin.

SUMMARY OF THE INVENTION

The effect of a bacterial extract cultured in a thermal water on regulating the vascularization and, in particular, an advantageous effect of reducing excessive vasodilation has now been demonstrated.

Thus, the present invention features the administration/topical application of at least one extract of a non-photosynthetic and non-fruiting filamentous bacterium cultured in a medium comprising at least one non-sulfurous mineral and/or thermal water as an agent useful for reducing the bags and/or dark circles around the eyes.

DETAILED DESCRIPTION OF BEST MODE AND SPECIFIC/PREFERRED EMBODIMENTS OF THE INVENTION

Bacterial Extract

The bacterial extracts according to the present invention are prepared according to a process comprising the culturing of at least one non-photosynthetic and non-fruiting filamentous bacterium in a medium comprising at least one non-sulfurous mineral and/or thermal water.

The bacteria are non-photosynthetic filamentous bacteria which comprise, in particular, the bacteria belonging to the order of the Beggiatoales and more particularly the bacteria belonging to the genera *Beggiatoa, Vitreoscilla, Flexithrix* or *Leucothrix*.

For implementing the invention, bacteria belonging to the genus *Vitreoscilla* are preferred, in particular bacteria of the species *Vitreoscilla filiformis*.

These bacteria, several of which have already been described, generally have an aquatic habitat and can be found in particular in sea waters or in thermal waters. Exemplary bacteria include:

*Vitreoscilla filiformis* (ATCC 15551)
*Vitreoscilla beggiatoïdes* (ATCC 43181)
*Beggiatoa alba* (ATCC 33555)
*Flexithrix dorotheae* (ATCC 23163)
*Leucothrix mucor* (ATCC 25107)
*Sphaerotilus natans* (ATCC 13338)

Preferably, the bacterium is that corresponding to the strain deposited at the ATCC under No. 15551.

The term "thermal water" means a hot or cold water which is used for its therapeutic powers or for a bathing use. It is possible to use a thermal water or a mineral water. Generally, a mineral water is suitable for consumption, which is not always the case with a thermal water. Each of these waters comprises, inter alia, dissolved minerals and trace elements. These waters are known to be employed for specific treatment purposes depending on the particular trace elements and minerals present therein.

Preferably, a thermal and/or mineral water is employed which exhibits a total mineral content of greater than or equal to 400 mg/l.

According to this invention, the term "total mineral content" means the sum of the concentrations of anions and cations present in the thermal or mineral water. In the thermal or mineral waters according to the invention, the total mineral content generally ranges from 400 to 900 mg/l.

The thermal and/or mineral water according to the invention can have a total mineral content of at least 700 mg/l, in particular a total concentration of carbonates and of bicarbonates of at least 150 mg/l and more preferably of at least 360 mg/l and in particular of sodium carbonate and bicarbonate of greater than 2 mg/l. The concentration of silicon oxide in the water used in the composition according to the invention can preferably be at least 6 mg/l and more preferably at least 9 mg/l.

The thermal water or the mineral water according to the invention can be selected from water from Vittel, waters from the Vichy basin, water from Uriage, water from La Roche Posay, water from La Bourboule, water from Enghien-les-Bains, water from Saint-Gervais-les-Bains, water from Néris-les-Bains, water from Allevard-les-Bains, water from Digne, water from Maizières, water from Neyrac-les-Bains, water from Lons-le-Saunier, water from Eaux-Bonnes, water from Rochefort, water from Saint Christau, water from Les Fumades and water from Tercis-les-Bains.

Among these waters, those which exhibit a total concentration of carbonates or bicarbonates of greater than 360 mg/l are water from Vittel, water from La Bourboule, water from Les Fumades, water from Enghien-les-Bains, water from La Roche Posay, water from the Vichy basin and water from Uriage.

Among these waters, those which exhibit a concentration of carbonates or bicarbonates of from 150 mg/l and 360 mg/l are water from Digne, water from Maizières, water from Rochefort or water from Saint Gervais-les-Bains.

Among these waters, those which comprise at least 2 mg/l of sodium carbonate or bicarbonate are water from La Roche Posay, water from Vittel, waters from the Vichy basin or water from Uriage.

The waters comprising at least 9 mg/l of silicon oxide are water from La Roche Posay, water from Vittel, waters from the Vichy basin or water from Uriage.

The thermal or mineral waters which are particularly suitable for the implementation of the invention have a concentration of calcium ions of greater than or equal to 100 mg/l, indeed even 140 mg/l.

According to one advantageous embodiment, the thermal or mineral water has a concentration of hydrogencarbonate ions of greater than or equal to 300 mg/l. The hydrogencarbonates, also known as bicarbonates, are present in particular at a concentration of greater than or equal to 350 mg/l.

According to another advantageous embodiment, the bacteria are cultured in a medium comprising at least one thermal water. The latter can in particular be selected from water from Vittel, waters from the Vichy basin, water from Uriage, water from La Roche Posay, water from La Bourboule, water from Les Fumades, water from Enghien-les-Bains or water from Eaux-Bonnes.

The waters which make it possible to obtain a particularly advantageous result according to the invention are selected in particular from water from La Roche Posay and water from Vittel, or a water with a similar composition.

Water from La Roche Posay is extracted from the spring of the same name; it is a water comprising bicarbonate, calcium, silicate and selenium. It generally comprises approximately 387 mg/l of bicarbonate ions, approximately 140 mg/l of calcium ions and at least 4 mg/l of sulfates.

Water from Vittel is rich in calcium and in mineral salts (841 mg/l) and comprises in particular 202 mg/l of calcium, 402 mg/l of bicarbonates and 336 mg/l of sulfates.

Culturing can in particular be carried out in the following medium:

| Composition: | Concentration: |
| --- | --- |
| Autolyzed yeast extract | 0.5 to 5 g/l |
| Plant peptone | 0.5 to 5 g/l |
| Anhydrous glucose | 0.5 to 7 g/l |
| Heller microelements | 0.5 to 5 ml/l |
| $CaCl_2 \cdot 10H_2O$ | 0.010 to 0.200 g/l |

The composition is made up to 1,000 ml with mineral and/or thermal water optionally topped with distilled or osmosed water.

Exemplary peptones include soybean papain peptone.

This medium is distinguished from the media generally used by the absence of catalase and sulfide.

The Heller microelements have been described by Heller, *Ann. Sci. Nat. Biol. Veg.*, 14, 1-223 (1953). They are mixtures of various mineral elements which are recommended by Heller not for the culturing of bacteria but for the nutrition of plant tissues cultured in vitro.

Culturing can be carried out at the appropriate temperature suitable for the bacterial species cultured. Generally, this temperature ranges from 18 and 40° C., depending on the strains. The pH of the culture medium preferably ranges from 5.5 to 8.

The composition of the Heller microelements, per 1 l of water, is as follows:

| | |
|---|---|
| $ZnSO_4 \cdot 7H_2O$ | 1 g |
| $MnSO_4 \cdot H_2O$ | 0.076 g |
| $CuSO_4 \cdot 5H_2O$ | 0.003 g |
| KI | 0.010 g |
| $H_3BO_3$ | 1 g |
| $AlCl_3 \cdot 6H_2O$ | 0.050 g |
| $NiCl_2 \cdot 6H_2O$ | 0.030 g |

Said thermal or mineral waters can replace all or part of the aqueous phase of the culture medium. They can thus be a mixture in any proportion with the water, in particular distilled or osmosed water, present in the culture medium. The mixture (i) of thermal water and (ii) of osmosed or distilled water could be in a ratio from 0.1% to 100%, especially from 0.1 to 50, in particular from 0.1 to 25.

After mixing all the elements of the medium, the culture medium comprising the thermal and/or mineral water is advantageously sterilized; this stage is carried out by methods known to one skilled in the art, such as sterilization by filtration or by heat.

The culture medium is subsequently inoculated with the bacteria.

The media most suitable for culturing bacteria are such that the thermal or mineral water preferably is at least 0.1% of the amount of water introduced for the preparation of the medium, in particular from 0.1 to 99.9%. Good results are obtained with concentrations of thermal water of approximately 1.33%, with respect to the osmosed and/or distilled water, for example from 0.5 to 20%, indeed even from 0.5 to 50%, but these concentrations can be increased without disadvantage.

In known fashion, the process for preparing the bacterial extract comprises at least one stage in which the bacteria are recovered at the end of culturing, in particular by separating them from the culture medium.

After culturing the bacteria, the biomass can be isolated by various known methods, for example by filtration, by coagulation with an alcohol (ethanol, isopropanol, isobutanol), by drying on a cylinder with a scraped precoat (starch, diatoms, and the like) or by freeze-drying. A preliminary concentration, for example at 80° C. under reduced pressure, improves this separation.

The biomass may be used alive or else be treated by various processes. An operation of rupturing the envelopes can be carried out, for example by the action of ultrasound. In addition, extracts can be prepared using an alcohol, such as ethanol or propanol.

Lipopolysaccharide extracts can also be prepared according to known methods; for example, see Noris and Ribbons, *Methods in Microbiology*, Vol. 5B, Academic Press (1971). The method generally used is the well-known "Westphal" method (or a related method), which consists in carrying out the extraction with phenol/water mixtures at 65° C. The extract is subsequently subjected to dialysis in order to remove the phenol.

The bacterial extract employed according to the invention may also result from the implementation of the following process: (i) at least one bacterium belonging to the order of the Beggiatoales is cultured in a medium comprising a monosaccharide as main carbon source and at least one mineral or thermal water and then (ii), after fermentation, the bacteria are separated from the culture medium in order to recover said mass of bacteria.

The bacteria recovered on conclusion of the fermentation stage can in particular be subjected to a stabilization and/or extraction treatment. It is the extract of filamentous bacteria which is thus obtained which will generally be used in or for the preparation of cosmetic or dermatological compositions. In a way known per se, the extract can thus be sterilized, in particular by filtration or by autoclaving.

The term "extract of non-photosynthetic filamentous bacteria" means equally well the supernatant from the culturing of said bacteria, the biomass obtained after culturing said bacteria or the extracts of the biomass which are obtained by treatment of this biomass.

In order to prepare the extracts according to the invention, said bacteria can be cultured according to the above process and can then be separated from the biomass obtained, for example by filtration, centrifuging, coagulation and/or freeze-drying.

Thus, after culturing, the bacteria are concentrated by centrifuging. The biomass obtained is autoclaved. This biomass can be freeze-dried in order to constitute what is referred to as the freeze-dried extract. Any freeze-drying method known to one skilled in the art can be used to prepare this extract.

The supernatant fraction from this biomass can also be filtered into a sterile container in order to remove the suspended particles. This supernatant fraction can also be decanted under sterile conditions into a sterile container. According to a specific embodiment of the invention, the supernatant fraction thus obtained is used as cosmetic or dermatological active principle.

The bacterial extracts according to the invention may be formulated in a suitable carrier in an amount of at least 20% by weight relative to the total weight of the composition, in particular in an amount of 0.001 to 20% by weight relative to the total weight of the composition and more particularly in an amount of 0.01 to 10% by weight relative to the total weight of the composition.

For certain applications or specific formulations, it may be advantageous to use high weight concentrations of bacterial extract, for example from 15 and 20%.

The bacterial extract cultured in a medium enriched with thermal water may also be used in the form of fractions of cellular components or in the form of metabolites. The microorganism(s), metabolite(s) or fraction(s) may also be introduced in the form of a freeze-dried powder, a culture supernatant and/or, where appropriate, in a concentrated form.

For certain applications, the living biomass may be used as is, for example in the form of masks or a poultice for producing an immediate effect.

According to the invention, the term "metabolite" is any substance derived from the metabolism of the microorganisms considered according to the invention and endowed with an efficacy for treating dark circles.

Unexpectedly, it has now been observed that the bacterial extracts cultured in thermal water were able to prove effective for regulating vascularization defects of the contour of the eyes and thus to prevent and/or reduce bags and/or dark circles around the eyes.

Specifically, it has now been demonstrated that the extract of the bacterium *Vitreoscilla filiformis* cultured in thermal water from La Roche Posay has an increased effectiveness in treating vascular disorders compared to the extract of the same bacterium cultured in a conventional medium, that is to say, without mineral or thermal water.

The main difference from these two extracts is in the procedures for preparing the culture medium where there is substitution of osmosed water by water from La Roche Posay. This leads in particular to a modification of the metabolism of the bacteria caused by an enrichment of the culture medium in mineral elements, particularly in selenium, strontium and zinc.

It is also interesting to note that the introduction of this biomass into a formulatory carrier does not present a risk of overexposure to these elements, since Se and Zn are elements that are essential to the body and Sr is widespread in food.

The table below provides the concentrations of these chemical elements in the bacterial extract according to the invention prepared according to the procedure of Example 1 (freeze-dried extract).

| | |
|---|---|
| Se (mg/kg) | 6 |
| Sr (mg/kg) | 10 |
| Zn (mg/kg) | 216 |

Thus, the application of this enriched extract leads to topical exposures of mineral salts per day of around:

| | |
|---|---|
| Se (µg/day) | 0.008 |
| Sr (µg/day) | 0.0032 |
| Zn (µg/day) | 0.094 |

It is noted here that the use of ions for improving skin condition is very old. Thus, dermatologically-targeted thermal cures on the banks of the Dead Sea—the saltiest expanse of water in the world—go back to ancient times (Abels D J et col, *Clinics in Dermatol.*, 14: 653-658, 1996). These baths exert an anti-pruriginous activity and it is not uncommon that people treated experience the feeling of having smoother and more supple skin (Even-Pazz Z, Isr *J. Med. Sci.*, 32: 11-15, 1996). To date, the advantage of the topical application of cations has been studied as much in the field of sensitivity as in that of skin dryness. Among the divalent cations, it is the calming effect of strontium which has been most documented (Hahn G S, In biochemical modulation of skin reactions. Kydonieus A F, Will J J (eds.), CRE, Boca Raton, Fla., US, 261-272, 2000).

Thus, the present invention features the cosmetic administration of at least one extract of a non-photosynthetic and non-fruiting filamentous bacterium cultured in a medium comprising at least one non-sulfurous mineral and/or thermal water as an agent useful for reducing the bags and/or dark circles around the eyes.

Moreover, the regime or regimen according to the invention advantageously makes it possible to reduce the hyperpigmentation of the suborbital region and/or lighten dark circles and to render the complexion of the region of the dark circles uniform with the remainder of the face.

The active bacterial extracts according to the invention are capable of acting on the vascular component of disorders of the eye contour, in particular of the dark circles and thus to make it possible to reduce the swelling and/or normalize the color of the dark circles.

The term "dark circle" means an area located around the eye, in particular underneath and in the inner side of the eye, that has a relief which is not in the continuity of the skin of the face, that is to say is a hollow or a bag (swollen area) and optionally with a color and/or a texture of the skin that is different from that of the rest of the face.

According to one alternative embodiment, it is possible to combine the bacterial extract used according to the invention with other agents, especially selected from retinoids or corticosteroids, free-radical scavengers, α-hydroxyacids or α-ketoacids or derivatives thereof, or else ion channel blockers.

The compositions according to the invention may also contain inert or even pharmacodynamically or cosmetically active additives or combinations of these additives, and in particular: wetting agents, depigmenting agents such as hydroquinone, azelaic acid, cafeic acid or kojic acid; emollients; moisturizers such as glycerol, PEG-400 or urea; anti-seborrheic agents or anti-acne agents, such as S-carboxymethylcysteine, S-benzylcysteamine, salts thereof and derivatives thereof, or benzoyl peroxide; antibiotics such as erythromycin and esters thereof, neomycin, clindamycin and esters thereof, tetracyclines; anti-fungal agents such as ketoconazole or 4,5-polymethylene-3-isothiazolinones; agents for promoting hair regrowth, such as minoxidil (2,4-diamino-6-piperidinopyrimidine 3-oxide) and derivatives thereof, diazoxide (7-chloro-3-methyl-1,2,4-benzothiadiazine 1,1-dioxide) and phenyloin (5,4-diphenylimidazoline-2,4-dione); non-steroidal anti-inflammatory agents, carotenoids, and in particular β-carotene; anti-psoriatic agents such as anthraline and derivatives thereof, and, finally, eicosa-5,8,11,14-tetraenoic acid and eicosa-5,8,11-trynoic acid, esters thereof and amides.

The composition according to the invention may also contain preservatives, such as para-hydroxybenzoic acid esters, stabilizers, moisture regulators, emulsifiers, UV-A and UV-B screening agents and antioxidants such as α-tocopherol, butylhydroxyanisole or butylhydroxytoluene.

Advantageously, said agents according to the invention could be incorporated into a system enabling their release at the eye contour, after application of the composition to the latter.

Said bacterial extract is present in the composition in an effective amount to obtain the desired effect, whether by regime or regimen, namely, a reduction in the dark circles and/or bags around the eyes.

This effect may be measured by simple visual observation or by comparative image analysis.

The compositions according to the invention may be for cosmetic or dermatological applications. Preferably, the composition of the invention is for cosmetic use to improve the appearance of the skin, in particular the appearance of the eye contour.

It will be, in particular, a composition for caring for and/or making-up dark circles and/or bags around the eyes.

It may be in any galenic form normally employed in the cosmetic and dermatological fields, suitable for oral or topical administration, preferably for topical administration onto the skin.

Unless indicted otherwise, within the context of the invention the term "skin" means any cutaneous surface of the body including the skin and expanded to the scalp and to the mucous membranes and semi-mucous membranes and the term "integuments" means the eyelashes, body hair, head hair and nails.

For topical application to the skin, the composition may be in the form of an optionally gelled aqueous, hydroalcoholic or oily solution, an emulsion of liquid or semi-liquid consistency of the milk type, obtained by dispersion of a fatty phase in an aqueous phase (O/W) or inversely (W/O), a triple emulsion (W/O/W or O/W/O), or a suspension or emulsion of soft, semi-solid or solid consistency of cream or gel type, a liquid, pasty or solid anhydrous product or else microemulsions, microcapsules, microparticles, or a vesicular dispersion of ionic type (liposomes or oleosomes) and/or of non-ionic type (niosomes) and/or a dispersion of nanospheres.

Said agent may be adsorbed or incorporated into structures made up of particles having a size that may range from 1 nm to a few μm (10 μm), for instance microcapsules, microparticles, vesicular dispersions of ionic type (liposomes or oleosomes) and/or of non-ionic type (niosomes) and/or dispersions of nanospheres. These particles may advantageously be porous and may be composed of silicates or aluminosilicates.

Examples of such formulations are described, in particular, in EP 1 99 636, EP 0 375 520, EP 0 447 318, EP 0 557 489, WO 97/12602, EP 1 151 741 or U.S. Pat. No. 5,914,126.

By way of example, the microspheres could be prepared according to the method described in EP 0 375 520.

The nanospheres could be in the form of an aqueous suspension and be prepared according to the methods described in FR 0015686 and FR 0101438.

The oleosomes consist of an oil-in-water emulsion formed by oily globules provided with a lamellar liquid-crystal coating dispersed in an aqueous phase (see, EP 0 641 557 and EP 0 705 593).

The agent according to the invention could also be encapsulated in nanocapsules consisting of a lamellar coating obtained from a silicone surfactant such as described in EP 0 780 115; the nanocapsules could also be prepared based on water-dispersible polyester sulfones according, for example, to the technique described in FR 0113337.

It is also possible to provide a composition in foam form or else in the form of a spray or an aerosol then comprising a pressurized propellant.

The composition may thus be in the form of a lotion, serum, milk, O/W or W/O cream, gel, ointment, pomade, powder, balm, patch, impregnated pad, soap, cake or foam.

Such a composition is generally in fluid or solid form. Consequently, such a composition may be in fluid form, in pasty form, in semi-solid form and in solid form, generally as a stick or as a dish, or have been deposited by coating onto a sheet of paper. Such a composition may be in the form of a foundation, for example in fluid form, in a pot or as a stick, or in the form of a tinted cream.

In particular, the care and/or makeup compositions according to the invention may be a cream, a gel, a serum for treating dark circles or a tinted cream, a foundation, preferably in a solid stick-type form preferably comprising coloring substances.

This invention also features compositions comprising at least one bacterial extract, in combination with at least one other agent, the effect of which will be to reinforce the action of said bacterial extract, for example by promoting skin microcirculation, which act, (i) via a stimulation of vasodilation and/or an anti-coagulant effect and/or an anti-hypertensive effect, and/or (ii) via a stimulation and/or the maintenance of angiogenesis, and/or (iii) via a stimulation of endothelium cell proliferation, and/or (iv) a stimulation of endothelium cell migration.

In particular, exemplary agents which act via (i) a stimulation of vasodilation and/or an anti-coagulant effect and/or an anti-hypertensive effect include:

antihypertensive agents; in particular potassium channel openers;
phosphodiesterase inhibitors;
flavonoids or flavoglycosides;
glucosides;
plant extracts with vasodilator properties;
vasodilator peptides that are not NO donors;
other vasodilators; and
temperature modulators.
Antihypertensive Agents:

Exemplary thereof are thiazides; angiotensin receptor inhibitors, such as losartan or candesartan; prostaglandins, particularly type E, and prostacyclins; ACE inhibitors, such as captopril or ramipril; potassium channel openers, such as minoxidil, cromakalim, diazoxide, nicorandil, pinacidil and derivatives; calcium channel blockers, such as nifedipine, verapamil, diltiazem, amlodipine; adrenergic receptor blockers, such as niacin (nicotinic acid), prazosine, hydralazine; muscarinic acetylcholine receptor activators.

Exemplary calcium channel blockers include:

agents that are active on the plasma membrane, that complex calcium and/or that are inhibitors of calcium entry, such as phenylalkylamines, for instance verapamil, anipamil, gallopamil, devapamil, falipamil, tiapamil, dihydropyridines, for instance nifedipine, amlodipine, dazodipine, felodipine, isradipine, lanicardipine, nimodipine, nimarketedipine, nitrendipine, ryosidine, benzothiazepines, for instance diltiazem, diphenylpiperazines, for instance cinnarizine, flunarizine; or agents that are active within the cell and are involved in the release of intracellular calcium stores or in the inhibition of the formation of the calcium/calmodulin complex. These are, for example, agents that are involved at the level of the sarcoplasmic reticulum, for instance dantrolene and TMB-8, calmodulin antagonists, for instance phenothiazine, trifluoperazine, chlorpromazine or naphthalene derivatives, or local anaesthetics such as dibucaine or dopamine antagonists such as pimozide, haloperidol or calmidazolium.

Also exemplary are manganese and/or salts that block calcium penetration into the cytoplasm in many cells.

Exemplary organic salts of manganese include manganese gluconate or manganese carbonate or manganese acetate or manganese citrate or manganese oleate or manganese oxalate.

Exemplary inorganic salts of manganese include mineral salts such as manganese chloride or manganese borate or manganese nitrate or manganese phosphate or manganese sulfate.

Preferably, use will be made of potassium channel openers, among which exemplary are:

ATP-dependent potassium channel openers, such as minoxidil, cromakalim, diazoxide, nicorandil, pinacidil or 2-cyano-1-(4-pyridyl)-3-(1,2,2-trimethylpropyl)guanidine of the family of the cyanoguanidines and derivatives thereof;

derivatives of benzopyran, of benzothiadiazine, of butenoic acid, of pyrimidine or of pyridine;

the compounds described in EP 0 886 515 corresponding to general formula (I):

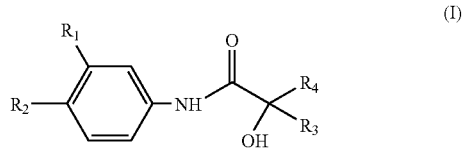

in which:

R1 is a cyano group, a halogen atom or an alkyl radical having from 1 to 4 carbon atoms, substituted with at least one halogen atom;

R2 is a cyano group or a halogen atom;

R3 is an alkyl radical having 1 or 2 carbon atoms, optionally substituted with at least one halogen atom;

R4 is a hydrogen atom or an alkyl radical having from 1 to 4 carbon atoms, substituted with at least one halogen atom, or an aryl radical, optionally substituted with one or more halogen atoms, or with one or more hydroxyl, carboxylic, nitro or cyano groups, linear or branched alkyl radicals having 1 to 4 carbon atoms, linear or branched alkoxy radicals having 1 to 4 carbon atoms, linear or branched alkanoyl radicals having 1 to 4 carbon atoms, or perfluoroalkyl radicals;

derivatives thereof and/or salts thereof.

As derivatives, exemplary are the compounds described in EP 0 915 857 and EP 0 916 652.

Phosphodiesterase Inhibitors:

Exemplary thereof are type V phosphodiesterase inhibitors, such as visnadine and esculoside, icarine and its derivatives or extracts containing same, as described in WO 2005/004858.

Flavonoids and Flavoglycosides:

Exemplary thereof are Ginkgo flavoglycosides, amentflavone or dimeric flavones of Gingko biloba in free form or in a form complexed with phospholipids, as described in WO 2005/004858; hesperidin, alpha-G-hesperidin, hesperidin methyl chalcone, rutosides (for example, beta-hydroxyethyl rutoside, trimethyl rutoside).

Glucosides:

Exemplary thereof are escin, escin beta-sitosterol, adenosine or ATP (adenosine triphosphate); esculoside, hesperidin.

Plant Extracts:

Exemplary thereof are extracts of everlast from Corsica (*Helichrysum italicum*) as described in particular in WO 03/018730; extracts of blackcurrant (*Ribes nigrum*), of mistletoe, of barrenwort (*Epimedium grandiflora*), of kiwi (*Actinidia chinensis* L.), of cypress (*Cupressus sempervirens*), of melilot (*Melissa officinalis*), of lesser periwinkle (*Vinca minora*), of *Centella asiatica*, of *Terminalia sericea* (sericoside), extracts of calendulae, extracts of arnica, extracts of *Ammi visnaga*.

Other Vasodilators:

Exemplary thereof are nicotinic acid (niacin) and its derivatives, such as nicotinic acid esters, for example, xanthinol nicotinate, inositol nicotinate; salicylic acid and its esters; dihydroergotoxin methanesulfonate; dihydroergocornine methanesulfonate, dihydroergocristine methanesulfonate, cinnarizine, vincamine, pentoxyfyline, bamethane sulfate, bencyclane hydrogen fumarate, beta-pyridylcarbinol.

Temperature Modulators:

As other means of activating skin microcirculation, it is also possible to modulate the temperature using agents and/or formulations with a thermal (heating or cooling) effect.

Menthol or plant extracts and/or essential oils of mint, of aloe vera or of ginseng are, for example, known as compounds with a freshening effect.

Camphor, plant extracts or essential oils of eucalyptus or of ginger, are, for example, known as examples of compounds with a heating effect.

These compounds are generally included at concentrations ranging from 0.1% to 10% of the total weight of the composition.

Agents for Promoting the Stimulation and/or Maintenance of Angiogenesis:

Exemplary thereof are:

extracellular matrix-remodeling proteases, which facilitate vessel growth, such as collagenases or MMPs (matrix metalloproteinases), for instance MMP-1 or interstitial collagenase; MMP-8 or neutrophile collagenase, MMP-13 or collagenase 3, gelatinases (for example MMP-2, MMP-9), stromelysins (MMP-3);

growth factors such as VEGF (vascular endothelial growth factor), PDGF (platelet derived growth factor); b-FGF (β-fibroblast growth factor); TGF-β (transforming growth factor TGF-β);

leptin and lipolytic hormones. Some hormones, such as adrenocorticotropin, melanocyte-stimulating hormone, luteotropic hormone and glucagon, cause a vasodilation-related mobilization of free fatty acids. The vasodilation may originate from substances released during lipolysis.

Agents for Promoting the Stimulation of Endothelial Cell Proliferation:

Exemplary thereof are:

nitric oxide (NO) donors or precursors, non-polymeric NO releasers,

NO synthase (NOS) synthesis and/or activity stimulators. Specific examples of such compounds are indicated above.

Agents for Promoting Endothelial Cell Migration:

Exemplary thereof are elastin-derived and angiotensin II-derived peptides.

Exemplary cosmetic active agents suitable for inclusion in the compositions of the invention include active agents useful for improving the appearance of the skin, in particular around the eye contour and the suborbital zone.

Such active agents are especially selected from among depigmenting agents, anti-pollution agents or free radical scavengers, tensioning agents, agents that stimulate the synthesis of dermal or epidermal macromolecules and/or that prevent their degradation, skin-relaxing agents, and mixtures thereof.

Depigmenting Agent:

Exemplary depigmenting or anti-pigmenting agents that can be incorporated into the compositions according to the present invention comprise, for example, the following compounds: kojic acid; ellagic acid; arbutin and derivatives thereof such as those described in EP 0 895 779 and EP 0 524 109; hydroquinone; derivatives of aminophenol such as those described in WO 99/10318 and WO 99/32077, and in particular N-cholesteryloxycarbonyl-para-aminophenol and N-ethoxycarbonyl-para-aminophenol; derivatives of iminophenol, in particular those described in WO 99/22707; L-2-oxothiazolidine-4-carboxylic acid or procysteine, and also salts and esters thereof; calcium D-pantetheine sulfonate, ascorbic acid and derivatives thereof, especially ascorbyl glucoside; and extracts of plants, in particular of liquorice, mulberry, skullcap and *Bacopa monnieri*, without this listing being limiting.

Anti-Pollution Agent or Free-Radical Scavenger:

The term "anti-pollution agent" means any compound capable of trapping ozone, monocyclic or polycyclic aromatic compounds such as benzopyrene and/or heavy metals such as cobalt, mercury, cadmium and/or nickel. The term "free-radical scavenger" means any compound capable of trapping free radicals.

Exemplary ozone-trapping agents that may be included in the compositions according to the invention include vitamin C and its derivatives, including ascorbyl glucoside; phenols and polyphenols, in particular tannins, ellagic acid and tannic acid; epigallocatechin and natural extracts containing it; extracts of olive tree leaf; extracts of tea, in particular of green tea; anthocyans; extracts of rosemary; phenol acids, in particular chlorogenic acid; stilbenes, in particular resveratrol; sulfur-containing amino acid derivatives, in particular S-carboxymethylcysteine; ergothioneine; N-acetylcysteine; chelating agents, for instance N,N'-bis(3,4,5-trimethoxybenzyl)ethylenediamine or one of its salts, metal complexes or esters; carotenoids such as crocetin; various starting materials, for instance the mixture of arginine, histidine ribonucleate, mannitol, adenosine triphosphate, pyridoxine, phenylalanine, tyrosine and hydrolyzed RNA, marketed by Laboratoires Sérobiologiques under the trademark CPP LS 2633-12F®, the water-soluble fraction of corn marketed by Solabia under the trademark PHYTOVITYL®, the mixture of extract of fumetory and of extract of lemon marketed under the trademark UNICOTROZON C-49® by Induchem, and the mixture of extracts of ginseng, of apple, of peach, of wheat and of barley, marketed by Provital under the trademark PRONALEN BIOPROTECT®.

Agents for trapping monocyclic or polycyclic aromatic compounds that may be incorporated in the compositions according to the invention include tannins such as ellagic acid; indole derivatives, in particular 3-indolecarbinol; extracts of tea, in particular of green tea, extracts of water hyacinths or *Eichornia crassipes*; and the water-soluble fraction of corn marketed by Solabia under the trademark PHYTOVITYL®.

Finally, exemplary heavy-metal-trapping agents that may be incorporated in the compositions according to the invention include chelating agents such as EDTA, the pentasodium salt of ethylenediaminetetramethylenephosphonic acid, and N,N'-bis(3,4,5-trimethoxybenzyl)ethylenediamine or one of its salts, metal complexes or esters; phytic acid; chitosan derivatives; extracts of tea, in particular of green tea; tannins such as ellagic acid; sulfur-containing amino acids such as cysteine; extracts of water hyacinth (*Eichornia crassipes*); and the water-soluble fraction of corn marketed by Solabia under the trademark PHYTOVITYL®.

The free-radical scavengers that may be incorporated in the compositions according to the invention comprise, besides certain anti-pollution agents mentioned above, vitamin E and its derivatives, such as tocopheryl acetate; bioflavonoids; coenzyme Q10 or ubiquinone; certain enzymes, such as catalase, superoxide dismutase and extracts of wheatgerm containing same, lactoperoxidase, glutathione peroxidase and quinone reductases; glutathione; benzylidenecamphor; benzylcyclanones; substituted naphthalinones; pidolates; phytantriol; gamma-oryzanol; guanosine; lignans; and melatonin.

Tensioning Agent:

The term "tensioning agent" means a compound capable of exerting tension on the skin, the effect of which is to temporarily smooth out irregularities on the skin's surface, such as wrinkles and fine lines.

Among the tensioning agents that can be incorporated in the compositions according to the present invention, exemplary are:

(1) synthetic polymers, such as polyurethane lattices or acrylic-silicone lattices, in particular those described in EP 1 038 519, such as a propylthio(polymethyl acrylate), propylthio(polymethyl methacrylate) and propylthio(polymethacrylic acid) grafted polydimethylsiloxane, or alternatively a propylthio(polyisobutyl methacrylate) and propylthio (polymethacrylic acid) grafted polydimethylsiloxane. Such grafted silicone polymers are marketed in particular by 3M under the trademarks VS 80, VS 70 or LO21, (2) polymers of natural origin, in particular (a) polyholosides, for example (i) in the form of starch derived in particular from rice, from corn, from potato, from cassava, from peas, from wheat, from oat, etc., or (ii) in the form of carrageenans, alginates, agars, gellans, cellulose-based polymers and pectins, advantageously as an aqueous dispersion of gel microparticles, and (b) latices consisting of shellac resin, sandarac gum, dammar resins, elemi gums, copal resins, cellulose-based derivatives, and mixtures thereof, (3) plant proteins and protein hydrolysates, in particular from corn, rye, wheat, buckwheat, sesame, spelt, pea, bean, lentil, soybean and lupin, (4) mixed silicates, especially phyllosilicates, and in particular laponites, (5) wax microparticles selected, for example, from carnauba wax, candelilla wax or esparto grass wax, (6) colloidal particles of inorganic filler having a number-average diameter of from 0.1 to 100 nm, preferably from 3 to 30 nm, and selected, for example from: silica, silica-alumina composites, cerium oxide, zirconium oxide, alumina, calcium carbonate, barium sulfate, calcium sulfate, zinc oxide and titanium dioxide.

Agent for Stimulating the Synthesis of Dermal or Epidermal Macromolecules and/or for Preventing their Degradation:

The cells of the dermis, in particular the fibroblasts, produce collagen, elastin and glycoprotein molecules. With the effect of age or else under the effect of UV rays, a notable decrease in these molecules occurs, along with degradation of collagen and elastin fibers due to the effect of collagenase or of elastase.

Among the active agents for stimulating the macromolecules of the dermis or preventing degradation thereof, exemplary are those that act:

either on the synthesis of collagen, such as extracts of *Centella asiatica*; asiaticosides and derivatives; ascorbic acid or vitamin C and its derivatives, such as its salts or its esters, in particular 5,6-di-O-dimethylsilyl ascorbate (marketed by Exsymol under the reference PRO-AA), the potassium salt of dl-alpha-tocopheryl-dl-ascorbyl phosphate (marketed by Senju Pharmaceutical under the reference SEPIVITAL EPC), ascorbyl magnesium phosphate, ascorbyl sodium phosphate (marketed by Roche under the reference STAY-C 50) and ascorbyl glucoside (marketed by Hayashibara); synthetic peptides, such as iamin, biopeptide CL or palmitoyloligopeptide marketed by Sederma; peptides extracted from plants, such as the soybean hydrolysate marketed by Coletica under the trademark PHYTOKINE®; plant hormones, such as auxins and lignans; the palmitoyl of lysine-threonine-lysine-serine pentapeptide marketed in particular under the trademark MATRIXYL by Sederma; dimethylaminoethanol; extracts of *Bupleurum chinensis* rhizome, such as those marketed under the trademarks PLEURIMINCYL or LIPOCARE by Sederma; acylated hydrolysates of wheat protein, in particular acylated with a palmitoyl group, such as that marketed under the trademark LIPACID PVB by Seppic; creatine; coenzyme Q10;

or on the synthesis of elastin, such as the extract of *Saccharomyces cerivisiae* marketed by LSN under the trademark CYTOVITIN®; and the extract of the alga *Macrocystis pyrifera* marketed by Secma under the trademark KELPADELIE®; melibiose; soybean proteins;

or on the synthesis of glycosaminoglycans, such as the product of fermentation of milk by *lactobacillus vulgaris*, marketed by Brooks under the trademark BIOMIN YOGOURTH®; the extract of the brown alga Padina pavonica marketed by Alban Müller under the trademark HSP3®; and the extract of *Saccharomyces cerevisiae* available in particular from the company Silab under the trademark FIRMALIFT® or from the company LSN under the trademark CYTOVITIN®;

or on the synthesis of fibronectin, such as the extract of the zooplankton Salina marketed by Seporga under the trademark GP4G®; the yeast extract available in particular from the company Alban Müller under the trademark DRI- ELINE®; and the palmitoyl pentapeptide marketed by Sederma under the trademark MATRIXIL®;

or on the inhibition of metalloproteinases (matrix metalloproteinases or MMPs) such as more particularly MMP 1, 2, 3 or 9. Exemplary are: retinoids and derivatives, oligopeptides and lipopeptides, lipoamino acids, the malt extract marketed by Coletica under the trademark COLLALI FT®; extracts of blueberry or of rosemary; lycopene; isoflavones, their derivatives or the plant extracts containing them, in particular extracts of soybean (marketed, for example, by Ichimaru Pharcos under the trademark FLAVOSTERONE SB®), of red clover, of flax, of kakkon or of sage;

or on the inhibition of serine proteases, such as leukocyte elastase or cathepsin G. Exemplary are: the peptide extract of leguminous plant (*Pisum sativum*) seeds, marketed by LSN under the trademark PARELASTYL®; heparinoids; and pseudodipeptides, such as {2-[acetyl-(3-trifluoromethylphenyl)amino]-3-methylbutyrylamino}acetic acid. Among the active agents for stimulating fillagrin and keratins, exemplary are the extract of lupin marketed by Silab under the trademark STRUCTURINE®; the extract of *Fagus sylvatica* beech buds marketed by Gattefosse under the trademark GATULINE®; and the extract of the zooplankton Salina marketed by Seporga under the trademark GP4G®.

Preferably, the agents for stimulating the synthesis of dermal or epidermal macromolecules and/or preventing degradation thereof are selected from among extracts of *Centella asiatica*, ascorbic acid and its derivatives, peptides extracted from plants, such as the soybean hydrolysate marketed by Coletica under the trademark PHYTOKINE®, or the extract of *Saccharomyces cerevisiae* marketed by LSN under the trademark CYTOVITIN®; the extract of the brown alga Padina pavonica marketed by Alban Müller under the trademark HSP3®; retinoids and derivatives; extracts of rosemary; the peptide extract of leguminous plant (*Pisum sativum*) seeds marketed by LSN under the trademark PARELASTYL®; {2-[acetyl-(3-trifluoromethylphenyl)amino]-3-methylbutyrylamino}acetic acid; extract of lupin; and mixtures thereof.

Muscle Relaxant or Dermo-Decontracting Agent:

The muscle relaxants or dermo-decontracting agents that can be incorporated into the compositions according to the invention comprise alverine and salts thereof, manganese gluconate, diazepam, the hexapeptide Argireline R marketed by Lipotec, carbonylated secondary and tertiary amines, adenosine, and also sapogenins and the natural extracts, in particular of wild yam, comprising them, and also the extracts of *Boswellia serrata*.

The present invention also features tinted compositions comprising the extracts of non-photosynthetic and non-fruiting filamentous bacterium cultivated in a medium comprising at least one non-sulfurous mineral and/or thermal water. In particular, it is a beige makeup composition for concealing dark circles.

Exemplary dyestuffs, include monochromatic pigments, nacres, reflective pigments that do or do not emit a color, interference pigments, liposoluble dyes, water-soluble dyes and mixtures thereof.

The liposoluble dyes are, for example, Sudan Red, DC Red 17, DC Green 6, β-carotene, soybean oil, Sudan Brown, DC Yellow 11, DC Violet 2, DC Orange 5 and quinoline yellow.

The pigments may be white or colored, mineral and/or organic, and coated or uncoated. Exemplary are the mineral pigments, of titanium dioxide, optionally surface-treated, zirconium or cerium oxides, and also iron or chromium oxides, manganese violet, ultramarine blue, chromium hydrate and ferric blue. Exemplary organic pigments include carbon black, D&C type pigments and lakes based on cochineal carmine or on barium, strontium, calcium or aluminum.

The nacreous pigments may be selected from among white nacreous pigments such as mica coated with titanium or with bismuth oxychloride, colored nacreous pigments such as titanium-mica with iron oxides, titanium-mica with, in particular, ferric blue or with chromium oxide, titanium-mica with an organic pigment of the aforementioned type and also nacreous pigments based on bismuth oxychloride.

The pigments may have undergone a surface treatment.

According to one particular embodiment of the invention, said agent included in the compositions of the invention is associated with at least one other agent that improves the appearance of the dark circles.

This agent is intended to reinforce the dark circle concealing effect obtained by the first agent and/or give the composition applied to the eye contour an optical effect that conceals dark circles and/or bags, replaced over time by the natural dark circle concealing effect provided by the first agent. The presence of the first agent in the composition also makes it possible to reduce the concentrations of the second agent that are normally effective for obtaining the desired effect on the dark circles, so as to promote the natural appearance of the makeup.

In particular, this agent is selected from:

an agent that acts on the lymphatic system;

a makeup agent useful for concealing the dark circles, otherwise known as a dark circle concealant;

and mixtures thereof.

Exemplary agents that act on the lymphatic system are the peptide inhibitors of the enzyme ACE (EC3.4.15.1) that convert angiotensin I to angiotensin II, such as the Val-Trp dipeptide. These ACE enzyme inhibitors have the effect of increasing the level of bradykinin and of thus promoting lymphatic drainage, while reducing water-retention problems.

Exemplary agents for concealing dark circles are "soft-focus" fillers, fluorescent agents, optical brighteners and mixtures thereof.

The term "soft-focus filler" means a filler which also gives transparency to the skin tone and a blurred effect. Preferably, the soft-focus fillers have an average particle size less than or equal to 15 microns. These particles may be of any shape and in particular may be spherical or non-spherical. More preferably, these fillers are non-spherical.

The soft-focus fillers may be selected from among silica and silicate powders, especially alumina powders, polymethyl methacrylate (PMMA) type powders, talc, silica/$TiO_2$ or silica/zinc oxide composites, polyethylene powders, starch powders, polyamide powders, styrene/acrylic copolymer powders, silicone elastomers, and mixtures thereof.

In particular, exemplary is talc having a number-average size less than or equal to 3 microns, for example talc having a number-average size of 1.8 microns and especially that marketed under the trademark TALC P3® by Nippon Talc, nylon-12 powder, especially that marketed under the trademark ORGASOL 2002 Extra D Nat Cos® by Atochem, silica particles surface-treated with a 1 to 2% mineral wax (INCI name: hydrated silica (and) paraffin) such as those marketed by Degussa, amorphous silica microspheres, such as those marketed under the trademark SUNSPHERE for example having the reference H-53 by Asahi Glass, and silica microbeads such as those marketed under the trademark SB-700® or SB-150® by Miyoshi, this list not being limiting.

The soft-focus filler may be present in the soft-focus cosmetic compositions in an amount ranging from 0.1 to 20% by weight and especially ranging from 1% to 12% by weight relative to the total weight of the composition, especially from 5 to 10%, for example around 8%.

The term "fluorescent agent" means a substance which, under the effect of ultraviolet rays and/or visible light, re-emits into the visible range the portion of light that it has absorbed in the same color that it reflects naturally. The naturally reflected color is thus reinforced by the re-emitted color and appears extremely bright.

Exemplary are colored resins of polyamide and/or of formaldehyde/benzoguanamine and/or of melamine/formaldehyde/sulfonamide, colored aminotriazine/formaldehyde/sulfonamide co-condensates and/or metallized polyester flakes and/or mixtures thereof. These fluorescent pigments may also be in the form of aqueous dispersions of fluorescent pigments.

Also exemplary are pink-colored fluorescent aminotriazine/formaldehyde/sulfonamide co-condensates having an average particle size of 3-4 microns, marketed under the trademark FIESTA ASTRAL PINK FEX-1 and the blue-colored fluorescent aminotriazine/formaldehyde/sulfonamide co-condensates having an average particle size of 3-4.5 microns marketed under the trademark FIESTA COMET BLUE FTX-60 by Swada or else the benzoguanamine/formaldehyde resins coated with formaldehyde/urea resin and colored yellow, marketed under the trademark FB-205 YELLOW and the benzoguanamine/formaldehyde resins coated with formaldehyde/urea resin and colored red, marketed under the trademark FB-400 ORANGE RED by UK Seung Chemical, the orange-colored polyamide resins marketed under the trademark FLARE 911 ORANGE 4 by Sterling Industrial Colors.

The fluorescent substances are preferably present in the composition in an amount ranging from 0.1 to 20%, preferably from 0.1 to 15%, more preferably from 0.5 to 3% by weight, relative to the total weight of the composition.

When the organic fluorescent substances are white, they are also known as optical brighteners.

The optical brightener has the effect of intensifying the radiance and brightening the tones of the cosmetic compositions comprising them upon application to the skin.

Among the optical brighteners, exemplary are stilbene derivatives, in particular polystyrylstilbenes and triazine stilbenes, coumarin derivatives, in particular hydroxycoumarins and aminocoumarins, oxazole derivatives, benzooxazole, imidazole, triazole, pyrazoline, pyrene derivatives and porphyrin derivatives and/or mixtures thereof.

Such compounds are, for example, available under the trademarks TINOPAL SOP® and UVITEX OB® from Ciba Geigy.

The preferred optical brighteners are sodium 4,4'-bis[(4,6-dianilino-1,3,5-triazin-2-yl)amino]stilbene-2,2'-disulfonate, 2,5-thiophendiylbis(5-tert-butyl-1,3-benzoxazole), disodium distyryl-4,4'-biphenyl sulfonate and/or mixtures thereof.

Examples of such compounds are described previously.

The present invention also features a cosmetic regime or regimen to improve the appearance of the eye contour, in which a composition such as defined above is topically applied to the eye contour and in particular to the suborbital zone.

This method is especially useful for reducing bags and/or dark circles around the eyes, in particular dark circles.

The compositions of the invention will preferably be topically applied to dark circles.

The compositions according to the invention may be applied daily as a day care product/makeup or as a night care product.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Preparation of a Bacterial Extract According to the Invention: Biomass of *Vitreoscilla filiformis* Cultured on a Medium Enriched with Thermal Water from La Roche Posay Preparation of the Culture Medium:
Composition:

| Yeast extract | 2 to 3 g |
| Soybean papain peptone | 2 to 3 g |
| Glucose | 2 to 3 g |
| Heller microelements | 2 ml |
| $CaCl_2 \cdot 2H_2O$ | 66.21 mg |
| Thermal water from La Roche Posay | 13-14 ml |

This stock solution will be diluted with osmosed water in a ratio of 1/75 before sterilization.

The pH of the medium is adjusted to 5.00 by adding a molar solution of $H_3PO_4$. The medium is sterilized by autoclaving at 121° C. for 30 minutes. After cooling to ambient temperature, the pH is readjusted to 7.20 by adding a molar solution of KOH.

Culturing:

After the medium has been inoculated at 1% with the *Vitreoscilla filiformis* strain, the culture is shaken on an orbital shaker at 100 rpm and at 26° C. After growth for 48 hours, the culture is centrifuged at 8,000 g for 15 minutes. The pellets are recovered and then autoclaved at 121° C. for 30 minutes. This biomass can be used for evaluation tests.

Example 2

Clinical Study

Clinical Data:

A first clinical study (study 1), double blind, evaluated intraindividually the comparative effect of a cream containing 5% of extract of *Vitreoscilla filiformis* (V. f.) cultured conventionally (hereinafter referred to as "conventional extract") on the red blotches occurring in individuals suffering from slight to moderate atopic dermatitis (symmetrical lesions versus placebo).

The "conventional" extract of *Vitreoscilla filiformis* is prepared according to the following modes:
Preparation of the Culture Medium:
Composition:

| Yeast extract | 2 g |
| Soybean papain peptone | 2 g |
| Glucose | 2 g |
| Heller microelements | 2 ml |
| $CaCl_2 \cdot 2H_2O$ | 66.21 mg |
| Water | qs 1 l |

The pH of the medium is then adjusted to 5.00 by adding a molar solution of $H_3PO_4$. The medium is sterilized by autoclaving at 121° C. for 30 minutes. After cooling to ambient temperature, the pH is readjusted to 7.20 by adding a molar solution of KOH.

Culturing:

In the laboratory: after the medium has been inoculated at 1% with the *Vitreoscilla filiformis* strain, the culture is shaken on an orbital shaker at 100 rpm and at 26° C. After growth for 48 hours, the culture is centrifuged at 8,000 g for 15 minutes. The pellets are recovered and then autoclaved at 121° C. for 30 minutes. This biomass can be used for evaluation tests.

In Fermenter:

In a fermenter preferably equipped with a draft tube in order to limit the shear force, the *Vitreoscilla filiformis* strain is inoculated at a minimum of 1% volume. The pH is kept stable at 7 UpH throughout the culturing, the T° is adjusted from 26 and 28° C. and the oxygenation is maintained at 10% $PO_2$ throughout the culturing, by the action either of the shaking speed or by adjustment of the air flow rate. This type of culturing can be carried out in batch, fed-batch or in continuous mode. The latter technique, which guarantees a reproducible biomass through controlling the growth rate (μ), will be preferred. The biomass harvested continuously by centrifugation at 10,000 g is frozen at −20° C. When the freezing tank is full, it is thawed at 4° C. and then packaged in packages that can be handled by an operator. These packages containing the biomass are then sterilized in order to be stabilized. This sterilization operation then is a production batch.

In the context of this study, the composition containing the "conventional extract" bacterial extract applied twice a day was very well tolerated.

The extract is formulated in composition 1A, which is a formula containing 5% of the conventional extract in an oil-in-water/Arlacel/Myrj emulsion containing 5% parleam and 15% volatile silicone. The effect of this composition 1A is compared with that of a placebo: composition 2A which corresponds to the excipient: oil-in-water/Arlacel/Myrj emulsion containing 5% parleam and 15% volatile silicone.

This composition 1A containing the "conventional extract" of *Vitreoscilla filiformis* at 5% did not have a significant effect on the vascular component of disorders of the skin of the individuals tested.

On the other hand, in a second study (study 2 carried out under the same conditions as the previous one and by the same team of experimenters), the composition containing 5% of *Vitreoscilla filiformis* extract cultured in a medium enriched with thermal water from La Roche Posay (according to Example 1) showed a specific effectiveness on the vascular component of the affection.

The extract is formulated in composition 1B, which is a formula containing 5% of bacterial extract according to the invention (obtained according to Example 1) in an oil-in-demineralized water Arlacel/Myrj emulsion containing 5% parleam, 15% cyclopentasiloxane, 3% glycerol and 2% petroleum jelly. The effect of this composition 1B is compared with that of a placebo: composition 2B which corresponds to an oil-in-water from La Roche Posay Arlacel/Myrj emulsion containing 5% parleam, 15% cyclopentasiloxane, 3% glycerol and 2% petroleum jelly.

In this study, the compositions are applied twice a day, the effectiveness was observed over the 15 days which followed the application.

Thus, the bacterial extracts cultured in water from La Roche Posay of composition 1B, unlike the known bacterial extracts, significantly reduced the skin manifestations associated with a vascular disorder (oedema) of the subjects in the areas where they were treated in comparison to the contra-lateral effect of the placebo (p=0.02, Fisher Test).

This superiority of the effectiveness from study 1 and study 2 is linked to a specificity to act on the vascular component of the skin manifestations in the individuals tested.

Specifically, the bacterial extracts cultured in the water from La Roche Posay (extract from Example 1) have significantly reduced the signs and symptoms due to a vasodilation of the patients in comparison with the contra-lateral effect of the placebo (p=0.02, Fisher Test).

Example 3

Formulations

Eye Contour Emulsion for Concealing Dark Circles:

| | |
|---|---|
| Bacterial extract from Example 1 | 1% |
| Soft-focus filler | 20% |
| Petroleum jelly | 4.00% |
| Sorbitan tristearate | 0.90% |
| Myristyl myristate | 2.00% |
| Methylparaben | 0.25% |
| Water | qs 100% |

The soft-focus filler contains 3% kaolin (USPBC colloidal kaolin from WCD International); 8% of silica microspheres (Silica Beads SB700 from Myoshi) and 10% of sericite (BC281 by Whittaker).

Foundation Stick for Concealing Dark Circles:

| | |
|---|---|
| Bacterial extract from Example 1 | 3.00 |
| Val-Trp dipeptide (acts on the lymphatic system) | 0.5 |
| Hydrogenated jojoba oil (Desert Whale) | 2.0 |
| Trimethylsiloxysilicate resin (KF-73125 from Shin Etsu) | 10.0 |
| Polyethylene wax (Polywax 500) | 15.0 |
| Iron oxide | 3.1 |
| Titanium oxide | 10.9 |
| Stearyl dimethicone | 7.0 |
| Sericite (S152 from Myoshi) | 6.0 |
| Cyclopenta(dimethylsiloxane) (viscosity 4 cst) | qs 100 |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic/dermatological method for reducing the bags and/or dark circles around the eyes of an individual afflicted therewith, the method comprising:

making a culture medium, which comprises adding (a) osmosed and/or distilled waters and (b) a second water comprising a total concentration of carbonates or bicarbonates of at least 150 mg/l, at least 6 mg/l of silicon oxide, at least 100 mg/l calcium ions, and at least 4 mg/l sulfates, wherein (b) is added in the range of 0.5 to 50 percent based on the amount of osmosed and/or distilled water of (a);

culturing a non-photosynthetic and non-fruiting filamentous bacterium in said medium to produce a culture of non-photosynthetic bacterium in said medium;

preparing a composition comprising between 0.001% and 20% by weight of an extract of said cultured bacterium; and topically administering to said individual an effective amount of said composition;

wherein said non-photosynthetic and non-fruiting filamentous bacterium is selected from the group consisting of *Vitreoscilla filiformis, Vitreocilla beggiatoides, Beggiatoa alba, Flexithrix dorotheae, Leucothrix mucor*, and *Speaerotilus natans*.

2. The cosmetic/dermatological method as defined by claim 1, wherein the method reduces hyperpigmentation of the suborbital region and/or lightening dark circles afflicting said individual.

3. The cosmetic/dermatological method as defined by claim 1, wherein the method renders the complexion of the region of the dark circles afflicting said individual uniform with the remainder of his or her face.

4. The cosmetic/dermatological method as defined by claim 1, wherein said extract is comprised in a concealer eye contour cream, a concealer eye contour gel or a concealer stick.

5. The cosmetic/dermatological method as defined by claim 1, said medium further comprising autolyzed yeast extract, plant peptone, anhydrous glucose, Heller microelements and calcium chloride.

6. The cosmetic/dermatological method as defined by claim 1, said at least one extract comprising Se, Sr and Zn.

7. A cosmetic/dermatological method for treating the vascular component of a disorder of the eye contour of an individual afflicted therewith, the method comprising:

making a culture medium, which comprises adding (a) osmosed and/or distilled waters and (b) a second water comprising a total concentration of carbonates or bicarbonates of at least 150 mg/l, at least 6 mg/l of silicon oxide, at least 100 mg/l calcium ions, and at least 4 mg/l sulfates, wherein (b) is added in the range of 0.5 to 50 percent based on the amount of osmosed and/or distilled water of (a);

culturing a non-photosynthetic and non-fruiting filamentous bacterium in said medium to produce a culture of non-photosynthetic bacterium in said medium;

preparing a composition comprising between 0.001% and 20% by weight of an extract of said cultured bacterium; and topically administering to said individual an effective amount of said composition;

wherein said non-photosynthetic and non-fruiting filamentous bacterium is selected from the group consisting of *Vitreoscilla filiformis, Vitreocilla beggiatoides, Beggiatoa alba, Flexithrix dorotheae, Leucothrix mucor*, and *Speaerotilus natans*.

* * * * *